US012709765B2

(12) United States Patent
Enriquez et al.

(10) Patent No.: US 12,709,765 B2
(45) **Date of Patent: *Aug. 18, 2026**

(54) CELLULOSE FOR BIOETHANOL PRODUCTION

(71) Applicant: SixRing Inc., Calgary (CA)

(72) Inventors: Alejandra Enriquez, Calgary (CA); Julie Greer, Calgary (CA); Markus Weissenberger, Calgary (CA); Alexandra Ostaszewski, Calgary (CA)

(73) Assignee: SixRing Inc., Calgary (CA)

( * ) Notice: Subject to any disclaimer, the term of this patent is extended or adjusted under 35 U.S.C. 154(b) by 222 days.

This patent is subject to a terminal disclaimer.

(21) Appl. No.: 18/460,219

(22) Filed: Sep. 1, 2023

(65) Prior Publication Data

US 2024/0294960 A1 Sep. 5, 2024

(30) Foreign Application Priority Data

Mar. 3, 2023 (CA) ................................ CA 3191789

(51) Int. Cl.

*C12P 7/10* (2006.01)
*C12P 7/06* (2006.01)
*C12P 19/02* (2006.01)
*C12P 19/14* (2006.01)

(52) U.S. Cl.

CPC ....... *C12P 19/02* (2013.01); *C12Y 302/01004* (2013.01); *C12Y 302/01021* (2013.01)

(58) Field of Classification Search

CPC .... C12P 7/10; C12P 19/14; C12P 7/14; C12P 7/06; C12Y 302/01004

See application file for complete search history.

(56) References Cited

U.S. PATENT DOCUMENTS 9,663,807 B2 5/2017 Narendranath et al.
9,920,309 B2 3/2018 Reisinger et al.
10,533,203 B2 1/2020 Carlson
10,876,141 B2 12/2020 Zavrel et al.
2013/0078698 A1* 3/2013 Lali .................... C08B 37/0057 568/426

FOREIGN PATENT DOCUMENTS

WO 9640970 A1 12/1996

OTHER PUBLICATIONS

"Cellulase adsorption on lignin: A roadblock for economic hydrolysis of biomass" from Saini et al. (Renewable Energy, vol. 98, Dec. 2016, pp. 29-42).

'Glucose production from cellulose through biological simultaneous enzyme production and saccharification using recombinant bacteria expressing the β-glucosidase gene' by Ichikawa S. et al, (J Biosci Bioeng. Mar. 2019;127(3):340-344).

'A novel facile two-step method for producing glucose from cellulose'(Bioresource Technology vol. 137, Jun. 2013, pp. 106-110).

'Dilute-acid Hydrolysis of Cellulose to Glucose from Sugarcane Bagasse' from Dussan et al. (Chemical Engineering Transactions vol. 38, 2014).

* cited by examiner

*Primary Examiner* — Maryam Monshipouri
(74) *Attorney, Agent, or Firm* — Berg Hill Greenleaf Ruscitti LLP

(57) ABSTRACT

A process to obtain glucose from a pretreated lignocellulosic biomass comprises providing a lignocellulosic biomass and contacting said lignocellulosic biomass to a modified Caro's acid composition for a period of time necessary to remove more than 98.5% of the lignin present in the lignocellulosic biomass and thus obtaining a solid stream and a liquid stream. The solid stream is exposed to an enzyme blend to produce a hydrolysate comprising sugars obtained from the hydrolysis of cellulose and hemicellulose. Optionally, the hydrolysate may be fermented to produce value-added products.

19 Claims, 4 Drawing Sheets

STARCH

CELLULOSE

Figure 1

CELLULOSE FOR BIOETHANOL PRODUCTION

CROSS REFERENCE TO RELATED APPLICATION

This application claims the benefit of and priority to Canadian Patent Application No. 3,191,789, filed Mar. 3, 2023. The entire specification and figures of the above-referenced application are hereby incorporated in its entirety by reference.

FIELD OF THE INVENTION

The present invention is directed to a novel process to generate glucose from cellulose, more specifically, a process which uses a specific cellulose in order to generate substantial improvement in conversion to glucose that can be further fermented into ethanol.

BACKGROUND OF THE INVENTION

Biofuel is increasingly becoming a necessity in order to wean off the human consumption of fossil fuels in aspects of everyday life, transport and home heating being the largest two industries of focus. As an alternative energy source to oil and coal, the main feedstock for bioethanol production is starch which can yield its sugar much more readily than cellulose. This is due to the difference in structure as starch links glucose molecules together through alpha-1,4 linkages and cellulose links glucose with beta-1,4 linkages. The beta-1,4 linkages allow for crystallization of the cellulose, leading to a more rigid structure which is more difficult to break down.

The limitation that comes from solely concentrating the bioethanol on extracting the sugars from starches prevents the utilization of the larger portion of biomass which comes in the form of lignocellulosic biomass (contains lignin, cellulose and hemicellulose) present in almost every plant on earth. A delignification reaction allows the recovery of cellulose from those lignocellulosic plants. Once the cellulose is separated from the other two biomass constituents i.e., lignin, and hemicellulose, further degradation of the cellulose generates oligosaccharides (i.e., glucose) which can be further processed to bioethanol.

Seen as a sustainable alternative to gasoline and with the goal of alleviating many countries' dependence on foreign oil, the bioethanol industry is still hampered by its dependence on corn or sugar cane as their main sources of biomass, as they are both rich in starch. It is estimated that about 45% of all corn production in the U.S. is directed to the ethanol fuel production. This is a situation which has disastrous consequences when the prices of gasoline go so low as to make corn-based biofuel unsustainable on a price viewpoint.

Across the world, many other large bioethanol-producing countries, including China and Brazil, have shown some struggles in ethanol production from biomass as many companies are carrying large debts from the implementation of such processes and large plants have been forced to shut down or decrease production.

In Asia, palm oil prices have recently increased to their highest levels in years, which, in turn, will hamper the ability of Indonesia and Malaysia to produce local biofuel. Oil palm trunk, which is a valuable and plentiful resource in those countries, contains a large amount of starch which is more readily solubilized in water, compared to cellulose. Starch can then be heated and hydrolyzed to glucose by amylolytic enzymes without pre-treatment. However, the conventional oil palm trunk treatment requires high capital and operational costs and is therefore prohibitive to market entry. Moreover, the treatment carries a high probability of microbial contamination during starch processing.

In Europe, the biofuel industry (both biodiesel and bioethanol production) depends heavily on food-based feedstocks like virgin vegetable oils (i.e., rapeseed, palm oil, soy) for biodiesel and corn, wheat, and sugar beet for bioethanol. Simultaneously, concerns have been raised that making fuel out of crops displaces other crops and can inflate food prices. These concerns are leading to policy changes that incentivize a shift away from food-based biofuels.

To pivot from starches to cellulose for the production of glucose is preferable as it will provide near-unlimited amount of feedstock from waste biomass and reduce the competition with food source feedstock to generate glucose. However, the costs to do so are currently prohibitive. Cellulosic ethanol as it is called relies on the non-food part of a plant to be used to generate ethanol. This would allow the replacement of the current more widespread approach of making bioethanol by using corn or sugarcane. The diversity and abundance of these types of cellulose-rich plants would allow to maintain food resources mostly intact and capitalize on the waste generated from these food resources (such as cornstalk) to generate ethanol. Other cellulose sources such as grasses, algae and even trees fall under the cellulose-rich biomass which can be used in generating ethanol if a commercially viable process is developed.

The reason why starches are preferred to cellulose-rich sources to generate ethanol is that extraction of glucose from cellulose is substantially more difficult and resource intensive. To better understand the difference which raises this difficulty it is worthwhile pointing the similarities and differences between starch and cellulose.

Cellulose and starch are polymers which have the same repeat units of glucose. However, the differences between starch and cellulose can be seen in the way the repeating glucose monomers are connected to one another. In starch, the glucose monomers are oriented in the same direction. In cellulose, each successive glucose monomer is rotated 180 degrees in respect of the previous glucose monomer. This, in turn, ensures that the bonds between each monomeric glucose differs between starch and cellulose. In starch, the bonds (otherwise known as links) are referred to as $\alpha$-1,4 linkages, in cellulose these bonds are referred to as $\beta$-1,4 linkages.

The difference between these bonds impacts the characteristics of starch and cellulose. Starch can dissolve in warm water while cellulose does not. Starch can be digested by humans, cellulose cannot. Starch is weaker than cellulose partly due to the fact that its structure is less crystalline than cellulose. Starch is, at its core, a method for plants to store energy, therefore extracting sugars from starch is much easier than to do so from cellulose as the latter's core function is to provide structural support.

As the main component of lignocellulosic biomass, cellulose is a biopolymer consisting of many glucose units connected through-1,4-glycosidic bonds (see FIG. 1). D-glucose is the building block of many polysaccharides, including cellulose. Glucose has two isomers: $\alpha$-glucose (present in starches as branched polymers) and $\beta$-glucose (present in cellulose as repeating units of $\beta$-glucose subunits connected via a $\beta$-1,4-glycosidic bond with one $\beta$-glucose monomer rotated by 180 degrees relative to its neighbour). A cellulose molecule can comprise between hundreds to thousands of glucose units. Since the cellulose molecules are linear, due in part to intermolecular hydrogen bonding, neighboring cellulose molecules can be very closely packed and, in turn, provide the structural strength needed to support plants.

Hydrolysis of Cellulose

The hydrolysis of cellulose to glucose is the rate limiting step in the conversion of cellulose into bioethanol. The processes currently using cellulose as a starting material for bioethanol production require the conversion of cellulose into oligomers, then glucose, prior to the ultimate generation of ethanol. The fermentation of glucose using yeast is what leads to the production of ethanol. While that last step in bioethanol production has been mastered for some time, the rate limiting step is the most crucial one and one which hinders a wider implementation of bioethanol. The difficulty in overcoming this conversion of cellulose into glucose lies with the fact that cellulose has a crystalline structure which renders its conversion to glucose quite difficult because of the close packing of multiple cellulose polymers. This close packing imparts on cellulose its inherent stability under a variety of chemical conditions. Cellulose polymers are generally insoluble in water, as well as a number of organic solvents. Cellulose is also generally insoluble when exposed to weak acids or bases.

In general, there are two main approaches to hydrolyze cellulose: chemical and enzymatic. The chemical method resorts to the use of concentrated strong acids to hydrolyze cellulose under conditions of high temperature and pressure. Many different types of acids, such as HCl and $H_2SO_4$, have been used in the past to achieve this. The use of one of these acids usually results in at least one of the following drawbacks: corrosion of the reaction vessel, difficulty of disposing of the discharged reactants, the cost of high energy intensive processes and others. The biofuel industry is generally reticent to use chemically hydrolyzed cellulose because of the presence of toxic by-products in the resulting glucose. These by-products, if introduced in the fermentation step, will negatively affect the delicate balance of the fermenting organism.

Cost of Enzymatic Hydrolysis

It is known that the costs to extract biofuel from cellulose are higher than when doing so from starch. It is estimated that, on average, depending on location and availability of biomass, the cost for cellulose conversion is about 50% more that starch conversion to glucose. This means that there currently is a clear barrier to producers for using cellulose rather than corn or other starch resources to generate glucose from biomass.

It is generally understood that roughly half of the total cost of producing biofuel from cellulose stems from the price of the enzymes (cellulases). The generation of enzymes for enzymatic hydrolysis of cellulose is a time-consuming process and large volumes of enzyme are required to render the process commercially viable. One possible approach is to improve the rate of the hydrolysis reaction which, in turn, would result in a decrease in the overall cost of the process.

The enzymatic approach to hydrolyzing cellulose uses enzymes to carry out the hydrolysis reaction. Enzymes, such as cellulases (comprising endo-1,4-β-glucanases: exo-1,4-β-glucanases; and β-glucosidases) require extensive controls in place to maximize the reaction rates the enzymatic approach is expected to provide. Temperature, pH, salinity, concentration of substrate and product are all factors that may affect enzyme activity. Small deviations from the enzyme's optimal conditions will result in loss of function. The conversion of cellulose to glucose is done by a few different enzymes: endo-1,4-β-glucanases; exo-1,4-β-glucanases; and β-glucosidases, all of which have specific environmental conditions which must be met. These controls as well as the cost of the enzymatic blends render the process cost prohibitive in some cases and/or limiting in their implementation.

PCT patent application WO9640970 (A1) discloses a method of producing sugars from materials containing cellulose and hemicellulose comprising: mixing the materials with a solution of about 25-90% acid by weight thereby at least partially decrystallizing the materials and forming a gel that includes solid material and a liquid portion: diluting said gel to an acid concentration of from about 20% to about 30% by weight and heating said gel to a temperature between about 80° C. and 100° C. thereby partially hydrolyzing the cellulose and hemicellulose contained in said materials: separating said liquid portion from said solid material, thereby obtaining a first liquid containing sugars and acid: mixing the separated solid material with a solution of about 25-90% acid until the acid concentration of the gel is between about 20-30% acid by weight and heating the mixture to a temperature between about 80° C. and 100° C. thereby further hydrolyzing cellulose and hemicellulose remaining in said separated solid material and forming a second solid material and a second liquid portion: separating said second liquid portion from said second solid material thereby obtaining a second liquid containing sugars and acid: combining the first and second liquids; and separating the sugars from the acid in the combined first and second liquids to produce a third liquid containing a total of at least about 15% sugar by weight, which is not more than 3% acid by weight.

U.S. Pat. No. 10,876,141 B2 describes a novel and advantageous process for the hydrolysis of biomass which enables a thorough hydrolyzation also of recalcitrant biomass such as sugar cane straw and sugar cane bagasse. Said process comprising the steps of a) contacting the biomass with an enzyme-composition containing at least one enzyme selected from the class of hydrolases in a vessel, b) separating a solid and a liquid phase, c) enzymatic conversion of the solid phase, and d) combining at least part of the converted solid phase of step c) with the liquid phase of step b).

U.S. Pat. No. 9,920,309 B2 is directed to an enzyme-composition for hydrolyzing biomass containing comprising at least one cellulase, at least one hemicellulases and/or at least one pectinases. In a further aspect, the present invention is directed to a process for hydrolyzing biomass implementing this enzyme-composition and the use of the enzyme-composition for hydrolyzing biomass.

U.S. Pat. No. 10,533,203 B2 discloses a system for treating biomass for the production of ethanol and a biorefinery for producing a fermentation product from biomass. The biorefinery comprises a system for preparing the biomass into prepared biomass and a system for pre-treating the biomass into pre-treated biomass. The biorefinery comprises a separator, a first treatment system, a second treatment system, and a fermentation system. A method for producing a fermentation product from biomass is disclosed.

In the paper entitled 'Glucose production from cellulose through biological simultaneous enzyme production and saccharification using recombinant bacteria expressing the β-glucosidase gene' by Ichikawa S. et al, (J Biosci Bioeng. 2019 March: 127(3):340-344), there is disclosed a cellulosic biomass saccharification technologies. Glucose was produced by the hydrolysis of 100 g/L Avicel cellulose for 10 days through biological simultaneous enzyme production and saccharification (BSES), and the product yield was similar to that obtained through BSES with purified β-glucosidase supplementation.

In the paper entitled "A novel facile two-step method for producing glucose from cellulose" (Bioresource Technology Volume 137, June 2013, Pages 106-110) a two-step acid-catalyzed hydrolysis methodology is disclosed where cellulose is hydrolyzed to glucose with high yield and selectivity under mild conditions. Its approach involves a multi-step hydrolysis, comprising as first step, the depolymerization of microcrystalline cellulose in phosphoric acid to cellulose oligomer at 50° C. The second step involves the precipitation of the oligomer by ethanol and subsequent hydrolysis with dilute sulfuric acid.

In the paper entitled "Dilute-acid Hydrolysis of Cellulose to Glucose from Sugarcane Bagasse" from Dussan et al. (CHEMICAL ENGINEERING TRANSACTIONS VOL. 38, 2014), there is disclosed a method of generating ethanol through the hydrolysis of cellulose. Sugarcane bagasse is used as a substrate for ethanol production, optimum conditions for acid hydrolysis of cellulose fraction were assessed. The glucose thus generated was fermented to ethanol using the yeast (Scheffersomyces *stipitis*).

In the paper entitled "Cellulase adsorption on lignin: A roadblock for economic hydrolysis of biomass" from Saini et al. (Renewable Energy, Volume 98, December 2016, Pages 29-42), there is disclosed the importance of a low lignin substrate for bioethanol production. It is highlighted how lignin inhibits access of enzymes to cellulose, which can lead in cases to the deactivation of enzymes for the saccharification process.

U.S. Pat. No. 9,663,807 discloses the preparation of ethanol by using lignocellulosic biomass such as corn stover which is pre-treated to remove C5 compounds (derived from hemicellulose), to leave C6 solids to be subsequently subjected to a simultaneous saccharification and fermentation (SSF) process. It was noted that simultaneous saccharification and fermentation could be performed at temperatures suitable for ethanol production by the yeast (e.g., about 37° C.) but this, in turn, was less than optimal for the cellulase enzyme. Consequently, the yields from such enzymes were lower because their activity was impeded by the presence of lignin on which cellulase enzymes could bind. In that case, it was discovered that addition of a lignin-binding agent, such as clarified thin stillage and/or Anaerobic Membrane Bioreactor (AnMBR) effluent could result in increased glucose yield during enzyme hydrolysis.

The hydrolysis of cellulose is, as seen from the above, limited by the structure of cellulose itself but also by the approaches taken to degrade it into a biofuel. The production of a robust, low-energy, low-cost process from lignocellulosic biomass has not yet been achieved.

In light of the above, there is a profound need to develop a process for biofuel generation from waste biomass as an abundant and untapped source of renewable biofuels that does not compete with a food source, such as corn. In that respect, a lignocellulosic biomass from which a low lignin content (also referred to as low Kappa number) cellulose is extracted is much more highly attractive as it will leave food sources available to fulfill their primary intended purpose and yet still generate a substantial cellulosic ethanol yield. The aforementioned is also substantiated with the tremendous efforts to convert waste biomass to biofuels using different approaches which have almost all failed to achieve this goal for subsequent conversion to glucose and ultimately, ethanol.

The inventors have surprisingly and unexpectedly found that the characteristics of the cellulose obtained from a specific type of delignification approach have a substantial impact on the downstream hydrolysis of said cellulose.

SUMMARY OF THE INVENTION

According to an aspect of the present invention, there is provided a process to obtain glucose from a pretreated lignocellulosic biomass, said process comprising the steps of:

- providing a lignocellulosic biomass
- exposing said lignocellulosic biomass to a modified Caro's acid composition for a period of time necessary to remove more than 98.5% of the lignin present in said lignocellulosic biomass and thus obtaining a solid stream and a liquid stream,
- exposing said solid stream to an enzyme blend to produce a hydrolysate comprising sugars obtained from the hydrolysis of cellulose and hemicellulose,
- optionally, fermenting said hydrolysate to produce value-added products.

In some embodiments of the present invention, the process of contact said lignocellulosic biomass to a modified Caro's acid composition can be carried out for a varying duration of time depending on the particle size of the biomass and the type of biomass being fed into the process. In some cases, the process can last from 2 to 20 hours depending on that characteristic. The process is preferably run at temperatures below 50° C., more preferably at temperatures below 40° C.

According to a preferred embodiment of the present invention, the solid stream comprises less than 15% of hemicellulose. Preferably, the solid stream comprises less than 10% of hemicellulose. More preferably, the solid stream comprises less than 5% of hemicellulose.

Preferably, said enzyme blend comprises of cellulases and hemicellulases.

According to another embodiment of the present invention, there is also disclosed a process to hydrolyze a modified Caro's acid delignified cellulose into glucose comprising the following steps:

- providing a reaction vessel;
- providing a cellulose source delignified using a modified Caro's acid in an aqueous medium, wherein said cellulose source has a kappa number of less than 10, more preferably less than 5 and even more preferably, less than 2,
- exposing said cellulose source to an enzyme blend that is capable of converting said cellulose into glucose, thus obtaining a saccharified solution; and
- optionally, exposing said saccharified solution to an organism, which converts said saccharified solution to value-added products.

According to a preferred embodiment of the present invention, said cellulose source also is substantially devoid of hemicellulose, where the term "substantially devoid of hemicellulose" refers to a cellulose source comprising of less than 15% hemicellulose, preferably less than 10% hemicellulose, more preferably less than 5% hemicellulose.

According to a preferred embodiment of the present invention, the process of exposing said cellulose source to said enzyme blend occurs at a temperature of less than 70° C. Preferably said process occurs at a temperature between 40° C. to 60° C. According to a preferred embodiment of the present invention, the process of exposing said cellulose source to said enzyme blend occurs for a period of time ranging from 1 to 168 hours, preferably between 24 and 144 hours, and more preferably between 48 and 120 hours.

According to another embodiment of the present invention, there is also disclosed a process to hydrolyze a modified Caro's acid delignified cellulose into glucose, and optionally other value-added products, comprising the following steps:

providing a reaction vessel;

providing a cellulose source delignified using a modified Caro's acid in an aqueous medium, wherein said cellulose source has a kappa number of less than 10, more preferably less than 5 and even more preferably, less than 2, exposing said cellulose source to an enzyme blend that is capable of converting said cellulose into glucose;

adding to said vessel an organism capable of converting the glucose into a value-added product.

According to a preferred embodiment of the present invention, said cellulose source also is substantially devoid of hemicellulose, where the term "substantially devoid of hemicellulose" refers to a cellulose source comprising of less than 15% hemicellulose, preferably less than 10% hemicellulose, more preferably less than 5% hemicellulose.

According to a preferred embodiment of the present invention, the process of exposing said cellulose source to said enzyme blend occurs at a temperature of less than 50° C. Preferably said process occurs at a temperature between 30° C. to 40° C. According to a preferred embodiment of the present invention, the process of exposing said cellulose source to said enzyme blend occurs for a period of time ranging from 1 to 96 hours, preferably between 24 and 72 hours.

Preferably, said enzyme blend comprises of cellulases and hemicellulases. More preferably, said enzyme blend comprises of at least one exo-glucanase, at least one endo-glucanase and at least one β-glucosidase.

According to a preferred embodiment of the present invention, said value-added product is ethanol.

According to a preferred embodiment of the present invention, the fermenting organism is a bacterium is selected from the group consisting of all species from the genera *Clostridium, Lactobacillus, Zymomonas, Bacillus*, and *Escherichia.*

According to a preferred embodiment of the present invention, the fermenting organism is a yeast is selected from the group consisting of all species from the genera *Saccharomyces, Candida*, Kloeckera, *Hanseniaspora, Brettanomyces, Pichia, Pachysolen, Schizosaccharomyces, Zygosaccharomyces, Kluyveromyces, Torulaspora* and *Lanchacea.*

According to an aspect of the present invention, there is provided a process to hydrolyze cellulose into glucose comprising the following steps:

providing a reaction vessel;

providing a cellulose source into said reaction vessel in an aqueous medium, wherein said source of cellulose has a content of hemicellulose of less than 15%, preferably less than 10% and more preferably less than 5%, and a kappa number of less than 10, more preferably less than 5, and even more preferably, less than 2;

exposing said cellulose source to an enzyme blend that is capable of converting said cellulose into glucose; and optionally, recovering the solution comprising glucose.

Preferably, said cellulose source is exposed to an enzyme blend for a period of 1 to 168 hours. Preferably, said cellulose source is exposed to an enzyme blend at a temperature not exceeding 70° C.

According to a preferred embodiment of the present invention, the process further comprises a step of exposing the glucose containing solution to an organism capable of converting glucose to said value added product, wherein said organism is selected from the group consisting of bacterium or fungi, or any combination thereof.

Preferably, the bacterium is selected from the group consisting of all species from the genera *Clostridium, Lactobacillus, Zymomonas, Bacillus*, and *Escherichia.*

Preferably, the fungi is selected from the group consisting of all species from the genera *Saccharomyces, Candida, Kloeckera, Hanseniaspora, Brettanomyces, Pichia, Pachysolen, Schizosaccharomyces, Zygosaccharomyces, Kluyveromyces, Torulaspora* and *Lanchacea.*

According to an aspect of the present invention, there is provided a process to convert cellulose into glucose, and optionally other value-added products, comprising the following steps:

providing a reaction vessel;

providing a cellulose source to said reaction vessel: wherein said source of cellulose having a content of hemicellulose of less than 15%, preferably less than 10% and more preferably less than 5%, and a kappa number of less than 10, more preferably less than 5, and even more preferably, less than 2;

exposing said cellulose source to an enzyme blend that is capable of converting said cellulose into glucose;

adding to said vessel an organism capable of converting the glucose into value-added products.

Preferably, said enzyme blend comprises of cellulases and hemicellulases. Preferably also, said enzyme blend comprises of at least one exo-glucanase, at least one endo-glucanase and at least one β-glucosidase. Preferably, said cellulose source is exposed to said enzyme blend and said organism for a period of 1 to 96 hours. Preferably, said cellulose source is exposed to said enzyme blend and said organism at a temperature not exceeding 50° C.

Preferably, said source of cellulose is characterized by an absence of prior exposure to bleaching chemicals selected from the group consisting of: sodium hydrosulphite ($Na_2S_2O_4$); pentasodium salt diethylenetriaminepentaacetic acid: amine borane $(CH_3)_3CNH_2—BH_3$; borane ammonia complex $BH_3—NH_3$; sodium percarbonate: formamidine sulphinic acid: sodium perborate; and chlorine dioxide.

According to a preferred embodiment of the present invention, the method of delignification of biomass material which yields a low lignin cellulose (also referred to as low kappa number cellulose and also referred to as modified Caro's acid delignified cellulose) used in the cellulose to glucose conversion experiments comprise:

the source of cellulose is a lignocellulosic biomass delignified by exposure to a modified Caro's acid composition selected from the group consisting of: composition A: composition B and Composition C;

wherein said composition A comprises:

sulfuric acid in an amount ranging from 20 to 70 wt % of the total weight of the composition;

a modifier component comprising an amine moiety and a sulfonic acid moiety selected from the group consisting of: taurine; taurine derivatives; and taurine-related compounds; and a peroxide:

wherein said composition B comprises:

an alkylsulfonic acid; and a peroxide: wherein the acid is present in an amount ranging from 40 to 80 wt % of the total weight of the composition and where the peroxide is present in an amount ranging from 10 to 40 wt % of the total weight of the composition;

wherein said composition C comprises:

sulfuric acid;

a two-part modifier component comprising:

a compound comprising an amine moiety:

a compound comprising a sulfonic acid moiety; and a peroxide:

for a period of time sufficient to remove substantially all of the lignin present on said biomass material. To alleviate the text, the above-described process can be referred to hereinafter as the modified Caro's acid delignification process, as well as the obtained cellulose can be referred to as modified Caro's acid delignified cellulose or "MCA cellulose" to indicate the method of delignification employed to obtain said cellulose.

Preferably, said sulfuric acid, said compound comprising an amine moiety and a sulfonic acid moiety and said peroxide are present in a molar ratio of no more than 15:1:1. Also preferably, said sulfuric acid and said compound comprising an amine moiety and a sulfonic acid moiety are present in a molar ratio of no less than 3:1.

According to a preferred embodiment of the approach to obtain low hemicellulose content and low lignin cellulose, said delignification lasts from 2 to 20 hours.

According to a preferred embodiment of the approach to obtain low hemicellulose content and low lignin cellulose, said delignification is carried out at temperatures below 50° C. Preferably, the delignification is carried out at temperatures below 40° C.

It is widely accepted that a kappa number is a reliable indication of lignin content in a pulp or cellulosic material. The higher the kappa number, the higher the lignin content is. The kappa number is a measure of the degree of fibrous pulp digestion and can be applied to determine lignin content. Its value can vary from 0 to over 100, where 0 indicates a practically lignin-free pulp (such as that found in bleached pulp) and where a kappa number of 60 is usually attained with a standard unbleached pulp. When the kappa number is 60, this is a rough indication that the lignin content is about 9%, when the kappa number is about 20, this would indicate a lignin content of approximately 2.8-3.0%. When the kappa number is about 27, the lignin content is approximately 4.0%.

According to a preferred embodiment of the present invention, the process generates cellobiose (or glucose) from a cellulose with low kappa number and low hemicellulose content, were said low kappa number and low hemicellulose content has the following characteristics: particle size ranging from 0-1000 microns, a content of hemicellulose of less than 15%, preferably less than 10%; and more preferably less than 5 wt. % of the total weight of the cellulose; and a kappa number of less than 10, more preferably less than 5, and even more preferably, less than 2.

It is understood by those skilled in the art, that high lignin concentrations in the cellulose portion, which can be enriched after dilute acid pretreatments, can lead to detrimental effects for the saccharification enzymes, which can be deactivated by the interaction with lignin and lead to lower-than-expected glucose yields. Additionally, high lignin content can also pose problems in the distillation process creating difficult to remove residues, which increases the OPEX of bioethanol facilities.

According to another aspect of the present invention, there is provided a process wherein said cellulose is characterized by an absence of prior exposure to bleaching chemicals selected from the group consisting of: sodium hydrosulphite ($Na_2S_2O_4$): pentasodium salt diethylenetriaminepentaacetic acid; amine borane $(CH_3)_3CNH_2$—$BH_3$: borane ammonia complex $BH_3$—$NH_3$: sodium percarbonate: formamidine sulphinic acid: sodium perborate; and chlorine dioxide. The presence of such compounds on a bleached cellulose may have a negative impact on the enzyme and/or yeast and thus affect the yield of cellulosic ethanol. According to a preferred embodiment of the present invention, the process utilizes a low lignin and low hemicellulose content cellulose which allows the cellulase enzyme to efficiently convert the cellulose into glucose. The person skilled in the art will understand that, in the context of the present application, where there is a reference to bleaching of pulp, it is to be understood that the bleaching refers to a separate and distinct step of pulp processing. Consequently, the pulp used according to a preferred process of the present invention, is intended on being a pulp which has not undergone a separate bleaching step post-delignification. Such a treatment step is understood to not be economically viable when the ultimate goal of the cellulose is to be used to generate ethanol.

BRIEF DESCRIPTION OF THE FIGURES

Features and advantages of embodiments of the present application will become apparent from the following detailed description and the appended figures, in which:

Figure 1:
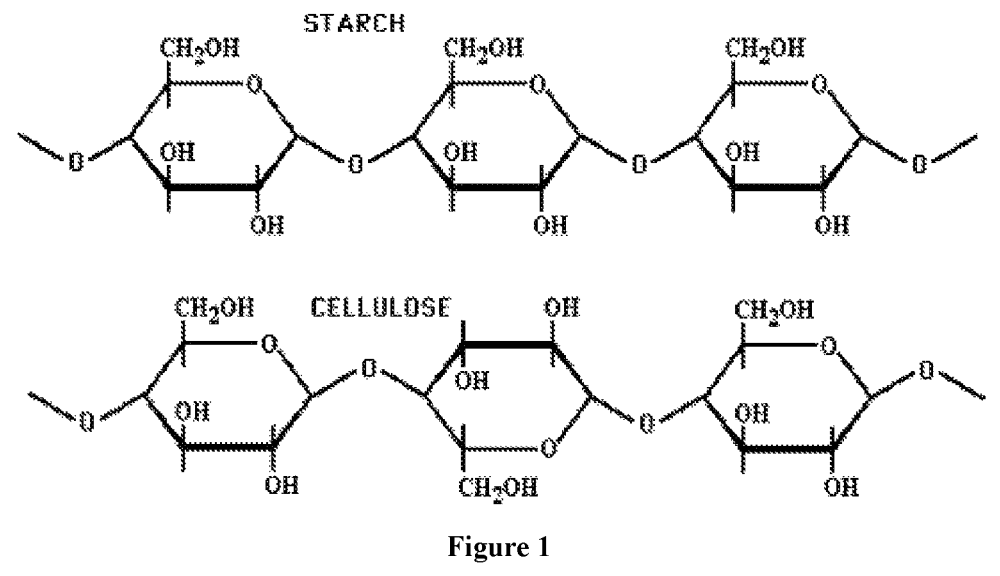

FIG. 1 is a depiction of glucose monomers present in a starch polymer and their $\alpha$-1,4-linkages compared to glucose monomers present in a cellulose polymer and their $\beta$-1,4-linkages:

DETAILED DESCRIPTION OF THE INVENTION

Figure 2:
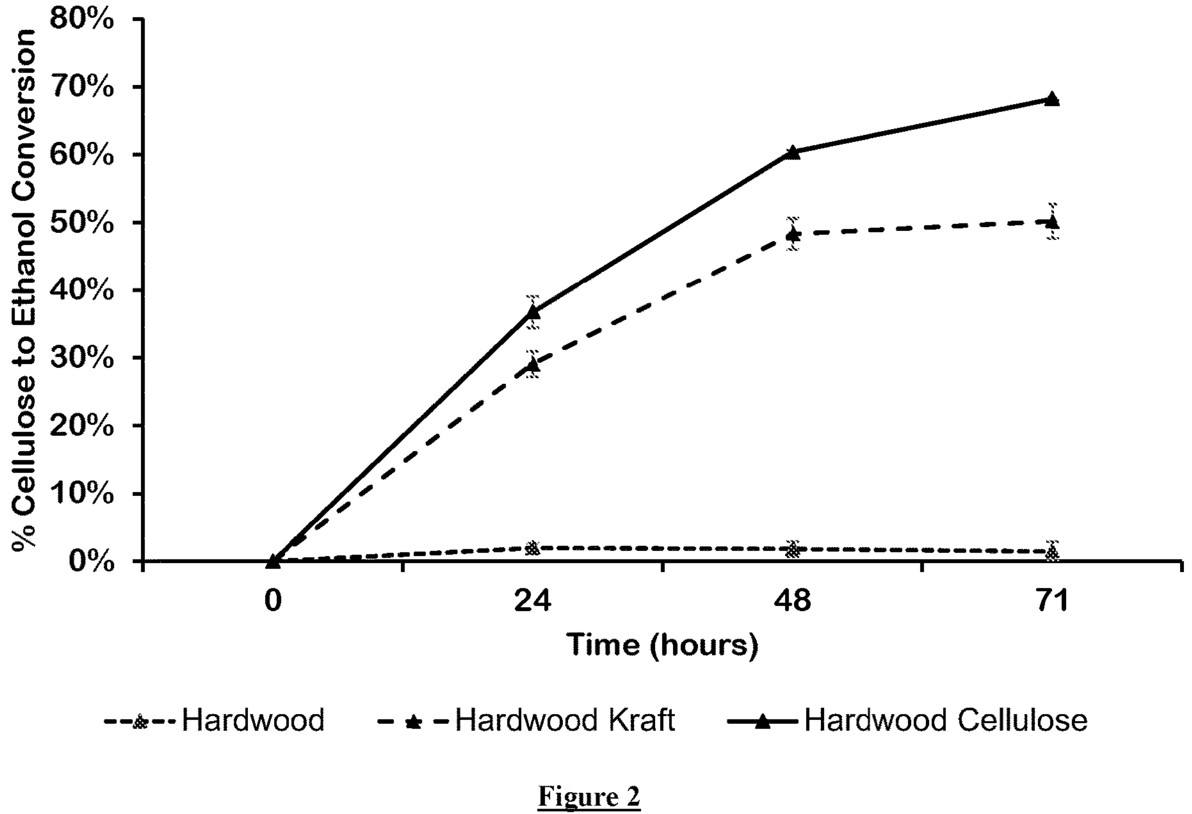
FIG. 2 illustrates a graphical representation of the ethanol conversion for various substrates obtained either by the Kraft process or by exposure to a modified Caro's acid (MCA)

The description that follows, and the embodiments described therein, is provided by way of illustration of an example, or examples, of particular embodiments of the principles of the present invention. These examples are provided for the purposes of explanation, and not limitation, of those principles and of the invention.

According to an aspect of the present invention, there is provided a process to obtain glucose from a pretreated lignocellulosic biomass, said process comprising the steps of:

providing a lignocellulosic biomass contacting said lignocellulosic biomass to a modified Caro's acid composition for a period of time necessary to remove more than 98.5% of the lignin present in said lignocellulosic biomass and thus obtaining a solid stream and a liquid stream, exposing said solid stream to an enzyme blend to produce a hydrolysate comprising sugars obtained from the hydrolysis of cellulose and hemicellulose, optionally, fermenting said hydrolysate to produce value-added products.

In some embodiments of the present invention, said lignocellulosic biomass may be mechanically treated to reduce particle size prior to contacting it to a modified Caro's acid.

In some embodiments of the present invention, the process of contact said lignocellulosic biomass to a modified Caro's acid composition can be carried out for a varying duration of time depending on the particle size of the biomass and the type of biomass being fed into the process. In some cases, the process can last from 2 to 20 hours depending on that characteristic. The process is preferably run at temperatures below 50° C., more preferably at temperatures below 40° C.

According to a preferred embodiment of the present invention, the solid stream comprises less than 15% of hemicellulose. Preferably, the solid stream comprises less than 10% of hemicellulose. More preferably, the solid stream comprises less than 5% of hemicellulose.

In some embodiments of the present invention, the process may further include a step to recover the liquid stream and upgrade it to value added products including fuels, industrial chemicals and/or energy.

According to a preferred embodiment of the present invention, the pH of solid stream is adjusted prior to being exposed to an enzyme blend. The pH of the obtained solid stream is adjusted to a value that is optimal for the enzyme blend. Preferably, the pH is adjusted to any value within the range between 3 to 7. Preferably, the pH is adjusted with any chemical known to those skilled in the art that can neutralize the modified Caro's acid. Preferably, the pH is adjusted with a hydroxide salt, such as ammonium hydroxide or sodium hydroxide.

According to a preferred embodiment of the present invention, said enzyme blend comprises of cellulases and hemicellulases. Preferably, said enzyme blend comprises of at least one exo-glucanase, at least one endo-glucanase and at least one β-glucosidase. More preferably, said enzyme blend also comprises at least one endo-xylanase and at least one β-xylosidase.

According to a preferred embodiment of the present invention, said enzyme blend is more efficient at hydrolyzing the modified Caro's acid solid stream, which has a kappa number of 0-10, preferably less than 5 and even more preferably, less than 2 than a Kraft cellulose with a kappa number of more than 10 or non-delignified lignocellulosic biomass with a kappa number of more than 50-100.

Those skilled in the art know that different value-added products can be obtained from the fermentation of sugar extracts or hydrolysates. The different value-added products are obtained when different fermenting organisms are employed. Examples of value-added products obtained from the fermentation of the hydrolysate obtained in the present invention include but are not limited to organic acids (i.e., formic acid, acetic acid), alcohols (i.e., ethanol, isopropanol, isobutanol, n-butanol, propanol), ketones (i.e., acetone), and combinations thereof. In a preferred embodiment of the present invention, the value-added product is ethanol.

According to another embodiment of the present invention, there is also disclosed a process to hydrolyze a modified Caro's acid delignified cellulose into glucose comprising the following steps:

providing a reaction vessel;

providing a cellulose source delignified using a modified Caro's acid in an aqueous medium, wherein said cellulose source has a kappa number of less than 10, more preferably less than 5 and even more preferably, less than 2, exposing said cellulose source to an enzyme blend that is capable of converting said cellulose into glucose, thus obtaining a saccharified solution; and optionally, exposing said saccharified solution to an organism, which converts said saccharified solution to value-added products.

According to a preferred embodiment of the present invention, said cellulose source also is substantially devoid of hemicellulose, where the term "substantially devoid of hemicellulose" refers to a cellulose source comprising of less than 15% hemicellulose, preferably less than 10% hemicellulose, more preferably less than 5% hemicellulose.

According to a preferred embodiment of the present invention, said aqueous medium has a pH of about 4.0 to 6.0. Preferably, said aqueous medium is maintained at a pH of 4.8-5.5.

According to a preferred embodiment of the present invention, the process of exposing said cellulose source to said enzyme blend occurs at a temperature of less than 70° C. Preferably said process occurs at a temperature between 40 to 60° C. According to a preferred embodiment of the present invention, the process of exposing said cellulose source to said enzyme blend occurs for a period of time ranging from 1 to 168 hours, preferably between 24 and 144 hours, and more preferably between 48 and 120 hours.

The term "saccharified solution" refers to a composition comprising of mostly simple sugars such as oligo, di-, and monosaccharides (i.e., glucose, xylose, etc.). In some embodiments, the term "saccharified solution" might also be referred to compositions where some complex sugars (i.e., polysaccharides including undegraded cellulose and hemicellulose) are present.

According to another embodiment of the present invention, there is also disclosed a process to hydrolyze a modified Caro's acid delignified cellulose into glucose, and optionally other value-added products, comprising the following steps:

providing a reaction vessel;

providing a cellulose source delignified using a modified Caro's acid in an aqueous medium, wherein said cellulose source has a kappa number of less than 10, more preferably less than 5 and even more preferably, less than 2, exposing said cellulose source to an enzyme blend that is capable of converting said cellulose into glucose;

adding to said vessel an organism capable of converting the glucose into value-added products.

According to a preferred embodiment of the present invention, said cellulose source also is substantially devoid of hemicellulose, where the term "substantially devoid of hemicellulose" refers to a cellulose source comprising of less than 15% hemicellulose, preferably less than 10% hemicellulose, more preferably less than 5% hemicellulose.

According to a preferred embodiment of the present invention, said aqueous medium has a pH of about 4.0 to 6.0. Preferably, said aqueous medium is maintained at a pH of 4.8-5.5.

According to a preferred embodiment of the present invention, the process of exposing said cellulose source to said enzyme blend occurs at a temperature of less than 50° C. Preferably said process occurs at a temperature between 30° C. to 40° C. According to a preferred embodiment of the present invention, the process of exposing said cellulose source to said enzyme blend occurs for a period of time ranging from 1 to 96 hours, preferably between 24 and 72 hours.

In referring to FIG. 2, one can notice the modified Caro's acid delignified cellulose with a lower kappa number and lower hemicellulose content have generated higher cellulose to ethanol conversion yields compared to that of Kraft cellulose. The enzyme blend exposure is meant to hydrolyze the β-1,4-glycosidic bonds of the cellulose to generate glucose. It is understood that the fermentation step of the process according to a preferred embodiment of the present invention is straightforward as it does not deviate from the common approach of glucose fermentation to value added products: preferably, ethanol. It is established that the first step is more determinant of the extent of biomass conversion to glucose which is subsequently employed in fermentation. It is imperative that the cellulose degradation to glucose be maximized at this step, otherwise it will prevent the second step of the process from having a significant impact.

According to a preferred embodiment of the present invention, it is observed that the ethanol yield is higher with the modified Caro's acid delignified cellulose than the ethanol yield when such is exposed to a Kraft hardwood cellulose (which has a kappa number=16), to a Kraft softwood cellulose (kappa number=28) or to the corresponding non-delignified biomass (kappa number >50-100). The modified Caro's acid delignified cellulose is obtained according to a process (or approach) to obtain low hemicellulose content and low lignin cellulose (also referred to as a low kappa number cellulose) as prepared according to a preferred process described hereinbelow and has a kappa number=0-5.

Process to Obtain a Low Kappa Number Delignified Cellulose

According to a preferred embodiment of the present invention, the method of delignification of biomass material which yields a modified Caro's acid delignified cellulose used in the cellulose to cellobiose (and ultimately, glucose) conversion experiments comprise:

- providing a biomass material comprising cellulose fibers and lignin;
- exposing said biomass material requiring delignification to a modified Caro's acid composition selected from the group consisting of: composition A: composition B and Composition C;
- wherein said composition A comprises:
  - sulfuric acid in an amount ranging from 20 to 70 wt % of the total weight of the composition;
  - a modifier component compound comprising an amine moiety and a sulfonic acid moiety selected from the group consisting of: taurine: taurine derivatives; and taurine-related compounds; and
  - a peroxide:
- wherein said composition B comprises:
  - an alkylsulfonic acid; and
  - a peroxide: wherein the acid is present in an amount ranging from 40 to 80 wt % of the total weight of the composition and where the peroxide is present in an amount ranging from 10 to 40 wt % of the total weight of the composition:
- wherein said composition C comprises:
  - sulfuric acid;
  - a two-part modifier component comprising:
    - a compound comprising an amine moiety:
    - a compound comprising a sulfonic acid moiety; and
  - a peroxide:

for a period of time sufficient to remove substantially all of the lignin present on said biomass material. The process can be carried out for a varying duration of time depending on the particle size of the biomass being fed into the process. The process can last from 2 to 20 hours depending on that characteristic. Moreover, the temperature of the resulting mixture also has an impact on the duration of the process as the reaction is highly exothermic, precautions are taken to prevent a runaway degradation of the cellulose. This would result in a carbon black resulting product with no value. The process is preferably run at temperatures below 50° C., more preferably at temperatures below 40° C. The process of delignification is preferably performed with a cooling means adapted to control the heat generated by the chemical reaction of delignification and maintain the temperature to avoid an undesirable 'runaway' reaction.

Preferably, said sulfuric acid, said compound comprising an amine moiety and a sulfonic acid moiety and said peroxide are present in a molar ratio of no more than 15:1:1. Preferably, for a modified Caro's acid comprising sulfuric acid, peroxide and taurine (as the modifier component), the molar composition is as follows: $H_2O$: $H_2O_2$: $H_2SO_4$: Taurine in a molar ratio of 56:10:10:1. Preferably, for a modified Caro's acid comprising TEOA/MSA, the molar composition is as follows: $H_2O$: $H_2O_2$: $H_2SO_4$:TEOA:MSA in a molar ratio of 56:10:10:1:1.

According to a preferred embodiment of the approach to obtain low lignin cellulose, said sulfuric acid and said compound comprising an amine moiety and a sulfonic acid moiety are present in a molar ratio of no less than 3:1.

Preferably, said compound comprising an amine moiety and a sulfonic acid moiety is selected from the group consisting of: taurine; taurine derivatives; and taurine-related compounds.

According to a preferred embodiment of the approach to obtain low lignin cellulose, said taurine derivative or taurine-related compound is selected from the group consisting of: taurolidine; taurocholic acid; tauroselcholic acid; tauromustine; 5-taurinomethyluridine and 5-taurinomethyl-2-thiouridine; homotaurine (tramiprosate); acamprosate; and taurates: as well as aminoalkylsulfonic acids where the alkyl is selected from the group consisting of $C_1$-$C_5$ linear alkyl and $C_1$-$C_5$ branched alkyl.

Preferably, said linear alkylaminosulfonic acid is selected form the group consisting of: methyl; ethyl (taurine); propyl; and butyl.

Preferably, branched aminoalkylsulfonic acid is selected from the group consisting of: isopropyl; isobutyl; and isopentyl.

According to a preferred embodiment of the approach to obtain low lignin cellulose, said compound comprising an amine moiety and a sulfonic acid moiety is taurine.

According to a preferred embodiment of the approach to obtain low lignin cellulose, said sulfuric acid and compound comprising an amine moiety and a sulfonic acid moiety are present in a molar ratio of no less than 3:1.

According to a preferred embodiment of the approach to obtain low lignin cellulose, said compound comprising an amine moiety is an alkanolamine is selected from the group consisting of: monoethanolamine: diethanolamine; triethanolamine; and combinations thereof.

According to a preferred embodiment of the approach to obtain low lignin cellulose, said compound comprising a sulfonic acid moiety is selected from the group consisting of: alkylsulfonic acids: arylsulfonic acids; and combinations thereof.

Preferably, said alkylsulfonic acid is selected from the group consisting of: alkylsulfonic acids where the alkyl groups range from $C_1$-$C_6$ and are linear or branched; and combinations thereof. More preferably, said alkylsulfonic acid is selected from the group consisting of: methanesulfonic acid; ethanesulfonic acid; propanesulfonic acid; 2-propanesulfonic acid; isobutylsulfonic acid; t-butylsulfonic acid; butanesulfonic acid; iso-pentylsulfonic acid; t-pentylsulfonic acid; pentanesulfonic acid; t-butylhexanesulfonic acid; and combinations thereof.

Preferably, said arylsulfonic acid is selected from the group consisting of: toluenesulfonic acid; benzesulfonic acid; and combinations thereof.

According to a preferred embodiment of the approach to obtain low lignin cellulose, said alkylsulfonic acid; and said peroxide are present in a molar ratio of no less than 1:1.

Preferably, said compound comprising a sulfonic acid moiety is methanesulfonic acid.

According to a preferred embodiment of the approach to obtain low lignin cellulose (i.e. MCA cellulose), said Composition C may further comprise a compound comprising an amine moiety. Preferably, the compound comprising an amine moiety has a molecular weight below 300 g/mol. Preferably also, the compound comprising an amine moiety is a primary amine. More preferably, the compound comprising an amine moiety is an alkanolamine. Preferably, the compound comprising an amine moiety is a tertiary amine. According to a preferred embodiment of the approach to obtain low lignin cellulose, the alkanolamine is selected from the group consisting of: monoethanolamine; diethanolamine; triethanolamine; and combinations thereof. Preferably, the alkanolamine is triethanolamine.

According to a preferred embodiment of the approach to obtain low lignin cellulose, said in Composition C, said sulfuric acid and said a compound comprising an amine moiety and said compound comprising a sulfonic acid moiety are present in a molar ratio of no less than 1:1:1.

Preferably, in Composition C, said sulfuric acid, said compound comprising an amine moiety and said compound comprising a sulfonic acid moiety are present in a molar ratio ranging from 28:1:1 to 2:1:1.

Preferably, in Composition C, said compound comprising an amine moiety is triethanolamine and said compound comprising a sulfonic acid moiety is methanesulfonic acid.

Experiment #1—Simultaneous Saccharification and Fermentation (SSF)

It is known by those skilled in the art that the saccharification and fermentation processes can be combined and performed simultaneously for ease of operation and to minimize downsides intrinsic to each process separately (i.e., formation and accumulation of fermentation inhibitors). During simultaneous saccharification and fermentation (SSF), temperatures are generally kept outside of optimal ranges for both the enzymes and the ethanologenic organism. This may come at the expense of saccharification and fermentation yields.

For this experiment, different types of biomass were utilized to determine the effect of the delignification using a modified Caro's acid. Said biomass types are as follows:

1. Hardwood Kraft cellulose
2. Hardwood cellulose delignified using the modified Caro's acid process described herein
3. Non-delignified Hardwood
4. Non-delignified Canola Straw
5. Canola cellulose delignified using the modified Caro's acid process described herein
6. Non-delignified Corn Stover
7. Corn Stover cellulose delignified using the modified Caro's acid process described herein Samples of lignocellulosic biomass were delignified as per a preferred method described herein comprising a modified Caro's acid. Said modified Caro's acid comprised 38.53% w/w of water, 14.46% w/w hydrogen peroxide, 42.69% w/w $H_2SO_4$ and 5.32% w/w of taurine. To that, the corresponding lignocellulosic biomass was added in a 5.0% w/w loading and the reaction was left for 20 hours at 37° C. After the reaction was considered complete, the substantially hemicellulose-free and lignin-free solid stream was filtered out from the liquid stream and neutralized to achieve a pH between 5-7. It will be known to those skilled in the art that the solid stream is not dry and will maintain a water content ranging from 10-90%. Said solid is referred to as "MCA cellulose", "cellulose" or "cellulose delignified using the modified Caro's acid process described herein". Said solid was placed in a vessel containing an aqueous medium at a pH of 5.3 at a loading of 5% w/w (oven dry) alongside a commercially available enzyme blend. The loading of the enzyme blend was that of 0.6 mg of enzyme/g of wet solids. To that, an ethanologenic organism (i.e., *Saccharomyces cerevisiae*) was added. The flasks were stoppered with fermentation airlocks to create an anaerobic environment to promote fermentation and incubated at 37° C., shaking at 150 rpm. Aliquots of the samples were collected every 24 hours to monitor the production of ethanol.

Figure 3:
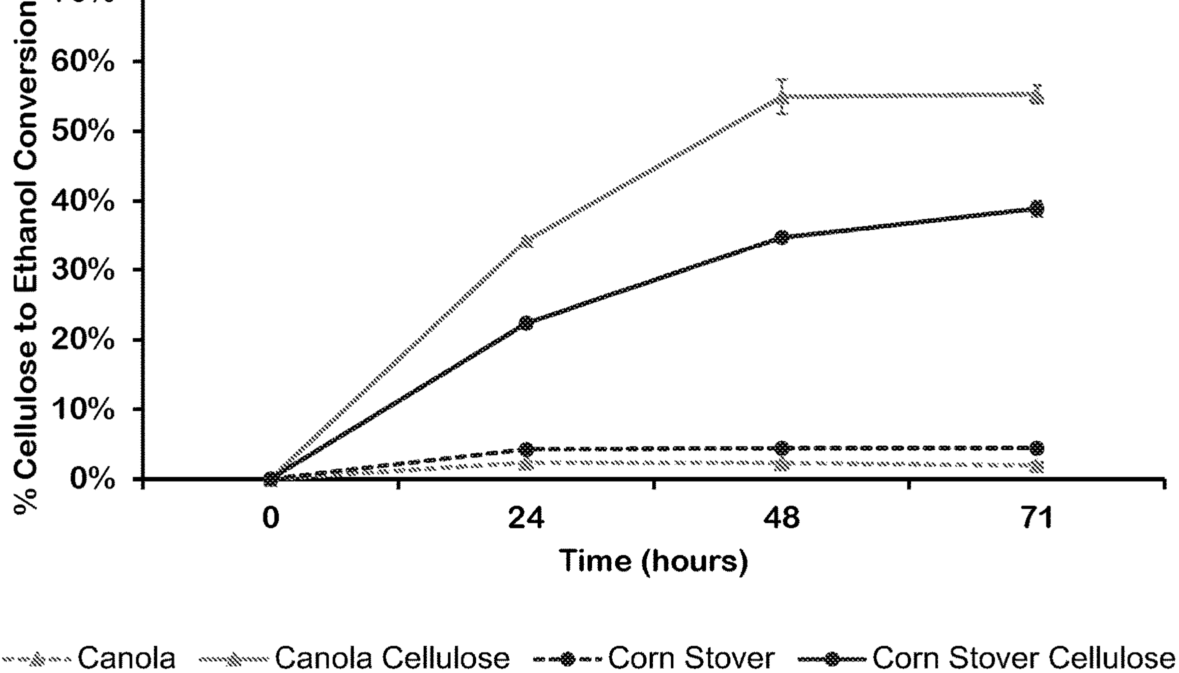
FIG. 3 is a graphical representation of the cellulose to ethanol conversion yields for modified Caro's acid delignified canola and corn stover cellulose in comparison to their non-delignified biomass counterparts.

FIGS. 2 and 3 demonstrates that ethanol conversion yields are higher with the modified Caro's acid delignified cellulose (i.e., the cellulose obtained as a result of the delignification of a lignocellulosic biomass component by a process employing a modified Caro's acid composition selected from the group consisting of: composition A: composition B and Composition C, as described hereinabove) than the ethanol yields when cellulose from the Kraft process or non-delignified biomass is used.

The modified Caro's acid delignified cellulose is obtained according to a process (or approach) which yields a low hemicellulose content and low lignin cellulose. The Kappa number for the Kraft hardwood is 16, whereas the Kappa number for the cellulose delignified employing a modified Caro's acid is less 2.

FIG. 2 shows that the modified Caro's acid delignified hardwood cellulose produced 18% more ethanol compared to Kraft hardwood and 65% more ethanol when compared to raw, non-delignified hardwood. In the same fashion, FIG. 3 demonstrates that the modified Caro's acid delignified canola straw and corn stover produced more than 50% and 35% more ethanol compared to their non-delignified counterparts, respectively.

Experiment #2—Separate Hydrolysis and Fermentation (SHF)

It is known by those skilled in the art that the hydrolysis and fermentation processes can also be performed separately, in order to allow for optimal hydrolysis/saccharification and fermentation conditions.

For this experiment, the following biomass types were selected to determine the advantages of the modified Caro's acid delignified cellulose. Said biomass types are as follows:

1. Hardwood Kraft cellulose
2. Hardwood cellulose delignified using a modified Caro's acid process described herein
3. Softwood Kraft cellulose
4. Softwood cellulose delignified using a modified Caro's acid process described herein Samples of lignocellulosic biomass were delignified as per a preferred method described herein comprising a modified Caro's acid. Said modified Caro's acid comprised 38.53% w/w of water, 14.46% w/w hydrogen peroxide, 42.69% w/w $H_2SO_4$ and 5.32% w/w of taurine. To that, the corresponding lignocellulosic biomass was added in a 5.0% w/w loading and the reaction was left for 20 hours at 37° C. After the reaction was considered complete, the substantially hemicellulose-free and lignin-free solid stream was filtered out from the liquid stream and neutralized to achieve a pH between 5-7. It will be known to those skilled in the art that the solid stream is not dry and will maintain a water content ranging from 10-90%. Said solid is referred to as "MCA cellulose", "cellulose" or "cellulose delignified using the modified Caro's acid process described herein". A loading of 5% (as oven dry) cellulose was placed in a vessel containing an aqueous medium at a pH of 5.3 alongside a commercially available enzymatic blend at a loading of 0.6 mg of enzyme/g of wet solids. The flasks were incubated at 50° C., shaking at 150 rpm. After a week of saccharification time, all samples were subjected to a fermentation step using *S. cerevisiae* as ethanologenic organism for a period of up to 48 hours.

Figure 4:
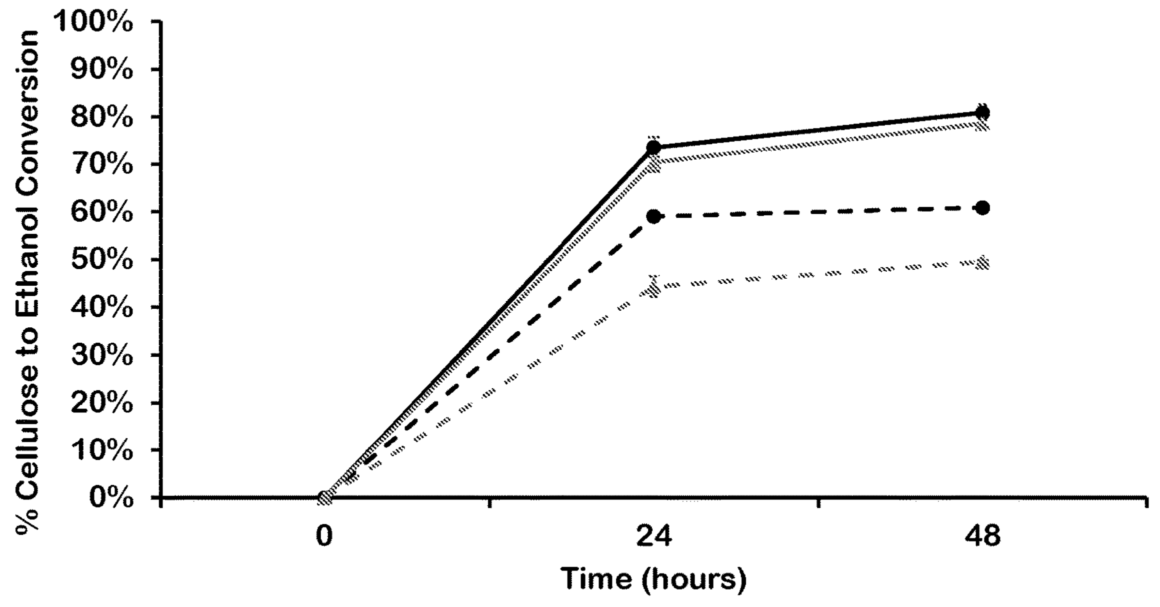
FIG. 4 is a graphical representation of ethanol yields for modified Caro's acid delignified hardwood and softwood cellulose in comparison to kraft hardwood and softwood pulps.

The results (FIG. 4) shows that the modified Caro's acid delignified cellulose with a lower kappa number and lower hemicellulose content have generated higher cellulose to ethanol conversion yields when compared to their Kraft counterparts. In the case of hardwood, the cellulose obtained from the delignification using a modified Caro's acid yielded a 20% difference in conversion yield in comparison to the Kraft version: whereas in the case of softwood, the increase was even more substantial at almost 30% difference in conversion yield between the MCA version and its Kraft counterpart.

According to a preferred embodiment of the process of the present invention, the process enables a higher conversion of cellulose to glucose, and sequentially ethanol, by overcoming the first step in the chain of reactions which is the conversion of cellulose to glucose.

It will be known by those skilled in the art that the process described herein provides significant benefits in comparison with existing state-of-the-art biomass delignification processes as it requires less energy due to the ambient conditions employed. In addition, the high delignification yields render the subsequent cellulose hydrolysis and fermentation highly efficient as the presence of lignin is known to be detrimental in currently existing processes due to residues in equipment and enzyme adsorption and deactivation. As a consequence to the lack of lignin, the resulting solids mostly comprising cellulose have a significantly higher surface area available to be degraded by enzymes and/or organisms, making this process highly efficient in terms yields (of both monomeric and oligomeric sugars as well as fermentation products) and more cost-effective.

Given this information, it is believed that idle ethanol plants located around the world could re-start operations of cellulose conversion to glucose (and subsequently, ethanol) if a biomass feedstock according to the following specifications was employed rather than using corn, sugar cane or conventional kraft pulp. Moreover, the implementation of a process according to a preferred embodiment of the present invention would essentially "dovetail" with the delignification process of a lignocellulosic biomass by using a modified Caro's acid, and the production of ethanol with the cellulose obtained from the delignification process. As mentioned previously, the person skilled in the art will recognize that by employing a cellulose obtained from a process using a modified Caro's acid, one will circumvent the need of any further or subsequent bleaching step following the delignification. It is to be understood that the bleaching refers to a separate and distinct step of pulp processing. Consequently, the pulp used obtained using a modified Caro's acid driven delignification process, is intended on being a pulp which has not undergone a separate bleaching step post-delignification. As is also understood by the person skilled in the art, such a treatment step (bleaching) is understood to not be economically viable when the ultimate goal of the cellulose is to be further converted in order to generate ethanol. It is also understood by a person skilled in the art that such a high purity, low kappa number cellulose will be beneficial for cellulosic ethanol processes as it minimizes the issues brought by the presence of lignin in Kraft pulp processes or unbleached cellulose. It is known to those skilled in the art that lignin causes issues during the treatment of the cellulose portion as well as during the distillation of the hydrolysate. By utilizing a low kappa number cellulose obtained from a process using a modified Caro's acid, one will circumvent those issues, which will lead to increased bioethanol yields.

While the foregoing invention has been described in some detail for purposes of clarity and understanding, it will be appreciated by those skilled in the relevant arts, once they have been made familiar with this disclosure that various changes in form and detail can be made without departing from the true scope of the invention in the appended claims.

The invention claimed is:

1. A process to obtain a value-added product from a lignocellulosic biomass, said process comprising the steps of:

providing a lignocellulosic biomass contacting said lignocellulosic biomass with a Caro's acid composition for a period of time necessary to remove more than 98.5% of the lignin present in said lignocellulosic biomass and thus obtaining a solid stream and a liquid stream, exposing said solid stream to an enzyme blend to produce a hydrolysate comprising sugars obtained from the hydrolysis of cellulose and hemicellulose, and fermenting said hydrolysate with a fermenting organism to produce a value-added product; and wherein said process is carried out at a temperature of less than 50° C.

2. The process according to claim 1 where the solid stream comprises less than 15% of hemicellulose.

3. The process according to claim 1 where the solid stream has a kappa number of less than 10.

4. The process according to claim 1 where said enzyme blend comprises of cellulases and hemicellulases.

5. The process according to claim 1 where said enzyme blend comprises of at least one exo-glucanase, at least one endo-glucanase and at least one β-glucosidase.

6. The process according to claim 1 where said value-added product is ethanol.

7. The process according to claim 1 where the fermenting organism is a bacterium is selected from the group consisting of all species from the genera *Clostridium, Lactobacillus, Zymomonas, Bacillus*, and *Escherichia.*

8. The process according to claim 1 where the fermenting organism is a yeast selected from the group consisting of all species from the genera *Saccharomyces, Candida, Kloeckera, Hanseniaspora, Brettanomyces, Pichia, Pachysolen, Schizosaccharomyces, Zygosaccharomyces, Kluyveromyces, Torulaspora* and *Lanchacea.*

9. A process to hydrolyze cellulose into glucose, said process comprising the following steps:

providing a reaction vessel;

providing a cellulose source into said reaction vessel in an aqueous medium, wherein said source of cellulose has a content of hemicellulose of less than 5%, and a kappa number of less than 2;

exposing said cellulose source to an enzyme blend that is capable of converting said cellulose into glucose;

optionally, recovering the solution comprising glucose; and wherein said process is carried out at a temperature of less than 50° C.

10. The process according to claim 9 where said enzyme blend comprises of cellulases and hemicellulases.

11. The process according to claim 9 where said enzyme blend comprises of at least one exo-glucanase, at least one endo-glucanase and at least one β-glucosidase.

12. The process according to claim 9 wherein said cellulose source is exposed to an enzyme blend for a period of 1 to 168 hours.

13. The process according to claim 9 further comprising a step of exposing the glucose containing solution to an organism capable of converting glucose to said value added product, wherein said organism is selected from the group consisting of bacterium or fungi, or any combination thereof.

14. The process according to claim 13 where said value added product is ethanol.

15. The process according to claim 13 where the bacterium is selected from the group consisting of all species from the genera *Clostridium, Lactobacillus, Zymomonas, Bacillus*, and *Escherichia*.

16. The process according to claim 13 where the fungi is selected from the group consisting of all species from the genera *Saccharomyces, Candida, Kloeckera, Hanseniaspora, Brettanomyces, Pichia, Pachysolen, Schizosaccharomyces, Zygosaccharomyces, Kluyveromyces, Torulaspora* and *Lanchacea*.

17. A process to convert cellulose into glucose, and optionally other value-added products, comprising the following steps:

providing a reaction vessel;

providing a cellulose source to said reaction vessel; wherein said source of cellulose having a content of hemicellulose of less than 5%, and a kappa number of less than 2;

exposing said cellulose source to an enzyme blend that is capable of converting said cellulose into glucose;

adding to said vessel an organism capable of converting the glucose into value-added products; and wherein said process is carried out at a temperature of less than 50° C.

18. The process according to claim 17 wherein said enzyme blend comprises of cellulases and hemicellulases.

19. The process according to claim 17 wherein said enzyme blend comprises of at least one exo-glucanase, at least one endo-glucanase and at least one β-glucosidase.

* * * * *